US00PP24005P2

(12) United States Plant Patent
Stemkens

(10) Patent No.: US PP24,005 P2
(45) Date of Patent: Oct. 29, 2013

(54) ***SAXIFRAGA* PLANT NAMED 'SAXZ0004'**

(50) Latin Name: *Saxifraga×arendsii*
Varietal Denomination: SAXZ0004

(75) Inventor: Henricus Godefridus Wilhelmus Stemkens, Enkhuizen (NL)

(73) Assignee: Syngenta Crop Protection AG, Basel (CH)

( * ) Notice: Subject to any disclaimer, the term of this patent is extended or adjusted under 35 U.S.C. 154(b) by 72 days.

(21) Appl. No.: 13/385,005

(22) Filed: Jan. 27, 2012

(51) Int. Cl.
*A01H 5/00* (2006.01)

(52) U.S. Cl.
USPC ..... Plt./263.1

(58) Field of Classification Search
USPC ..... Plt./263.1
See application file for complete search history.

*Primary Examiner* — Kent L Bell
(74) *Attorney, Agent, or Firm* — Joshua L. Price

(57) ABSTRACT

A new *Saxifraga* plant named 'SAXZ0004' particularly distinguished by the white flat-well opened flowers, light green pubescent foliage, with compact and mounded plant habit.

1 Drawing Sheet

Latin name of the genus and species of the plant claimed: *Saxifraga×arendsii*.

Varietal denomination: 'SAXZ0004'.

BACKGROUND OF THE NEW PLANT

The present invention comprises a new *Saxifraga*, botanically known as *Saxifraga×arendsii*, and hereinafter referred to by the variety name 'SAXZ0004'.

'SAXZ0004' is a product of a planned breeding program. The new cultivar has white flat-well opened flowers, light green pubescent foliage, with compact and mounded plant habit.

'SAXZ0004' originates from an open pollination made in a controlled breeding program in a greenhouse in Enkhuizen, Netherlands. The female parent was the proprietary plant designated 'H1059-51', unpatented, with white flowers, long peduncles, and a vigorous upright habit.

The male parent of 'SAXZ0004' was an unknown plant. The resultant seed were sown in August 2005 in Enkhuizen, Netherlands.

'SAXZ0004' was selected as one flowering plant within the progeny of the stated cross in March 2006 in a controlled environment in Enkhuizen, Netherlands.

The first act of asexual reproduction of 'SAXZ0004' was accomplished when vegetative cuttings were propagated from the initial selected plant in March 2006 in a controlled environment in Enkhuizen, Netherlands.

BRIEF SUMMARY OF INVENTION

Horticultural examination of plants grown from cuttings of the plant initiated in March 2006 in Enkhuizen, Netherlands, and continuing thereafter, has demonstrated that the combination of characteristics as herein disclosed for 'SAXZ0004' are firmly fixed and are retained through successive generations of asexual reproduction.

'SAXZ0004' has not been observed under all possible environmental conditions. The phenotype may vary significantly with variations in environment such as temperature, light intensity and day length.

A Plant Breeder's Right for this cultivar was applied for in the European Union on May 19, 2011, No. 2011/1306. 'SAXZ0004' has not been made publicly available more than one year prior to the filing of this application.

The following traits have been repeatedly observed and are determined to be basic characteristics of the new variety. The combination of these characteristics distinguishes this *Saxifraga* as a new and distinct variety.

BRIEF DESCRIPTION OF THE PHOTOGRAPHS

The accompanying photographic drawing shows typical flower and foliage characteristics of 'SAXZ0004' with colors being as true as possible with an illustration of this type.

Figure 1:
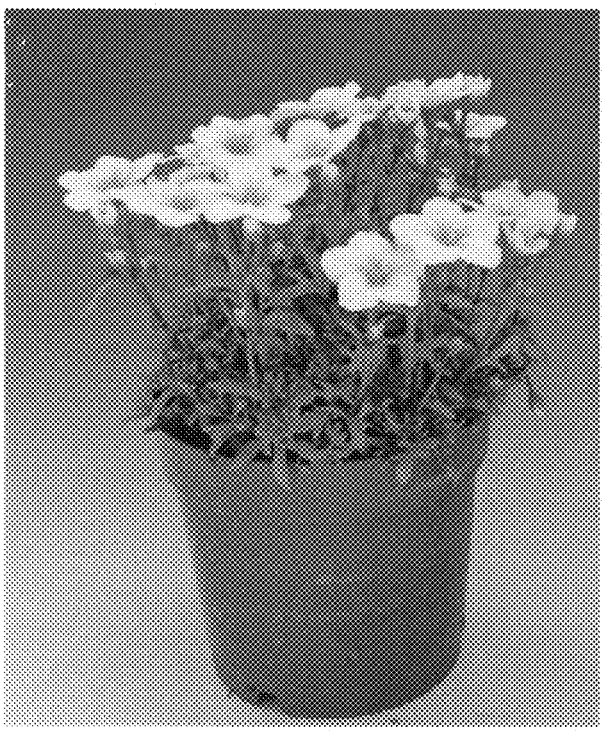
Figure 2:
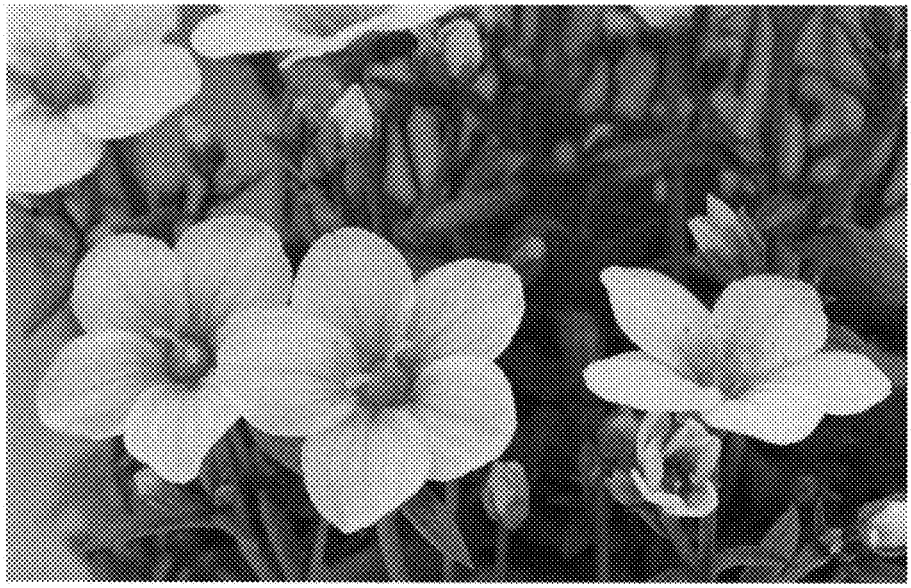

The photographic drawing shows in FIG. 1 a flowering plant of the new variety, and in FIG. 2 a close-up of the flowers.

DETAILED BOTANICAL DESCRIPTION

The plant descriptions, measurements and aforementioned photographs were taken in Enkhuizen, Netherlands in March 2011. Plants were growing in 11 cm containers and were 28 weeks of age.

Color Chart used: Royal Horticultural Society Colour Chart (R.H.S.) 2001

TABLE 1

DIFFERENCES BETWEEN THE NEW VARIETY 'SAXZ0004' AND A SIMILAR VARIETY

| | 'SAXZ0004' | 'Rocklarwhi' (U.S. Plant Pat. No. 20,257) |
|---|---|---|
| Peduncle length: | Shorter | Longer |
| Flower shape: | Flat open flowers | Petals curling a bit backwards |
| Plant habit: | More compact | More vigorous and upright |

Plant:

*Form, growth and habit*.—Short and compact creating mats of rosettes; each rosette develops several short stems and flower stems, with one or more inflorescences.

*Plant height.*—10.0 cm.
*Plant height (inflorescence included).*—13.0 cm.
*Plant width.*—13.0-15.0 cm.

Roots:
*Number of days to initiate roots.*—About 12-14 days at about 18 degrees C.
*Number of days to produce a rooted cutting.*—About 4 weeks at 18 degrees C.
*Type.*—Fine, fibrous, free branching.
*Color.*—Closest to RHS 155C.

Foliage:
*Type.*—Alternate.
*Immature, leaf color, upper surface.*—RHS 143C.
*Lower surface.*—RHS 143D.
*Mature, leaf color, upper surface.*—RHS 143C.
*Lower surface.*—RHS 143D.
*Length.*—1.0-1.7 cm.
*Width.*—0.5-1.6 cm.
*Shape.*—Ligulate.
*Base shape.*—Attenuate.
*Apex shape.*—Acute.
*Margin.*—Entire.
*Texture, upper surface.*—Pubescent.
*Lower surface.*—Pubescent.
*Color of veins, upper surface.*—RHS 143C.
*Color of veins, lower surface.*—RHS 143D.
*Petioles color.*—RHS 143D.
*Petioles length.*—0.4-0.6 cm.
*Diameter of petiole.*—0.2 cm.
*Texture.*—Pubescent.
*Color of lateral branches.*—RHS 143C.
*Length of lateral branches.*—0.2-0.4 cm.
*Diameter of lateral branches.*—0.2 cm.
*Length of internodes.*—0.5 cm.
*Texture.*—Slightly pubescent with short hairs.
*Peduncle color.*—RHS 143C.
*Length of peduncle.*—5.0 cm.
*Peduncle diameter.*—0.1 cm.
*Texture.*—Slightly pubescent.
*Color of pedicel.*—RHS 143C.
*Length of pedicel.*—0.3-0.5 cm.
*Diameter of pedicel.*—0.1 cm.
*Texture.*—Pubescent.

Inflorescence:
*Type.*—Simple cyme.
*Quantity of flower stems per rosette.*—2-3.
*Quantity of flowers per flower stem.*—2-7.
*Number of flowers per plant.*—150.
*Lastingness of individual blooms on the plant.*—10 days.
*Lastingness of an entire inflorescence.*—10-12 days.
*Natural flowering season in Europe.*—February-May in Europe, depending on climatic conditions.

Bud (when first showing color):
*Color.*—RHS 157D with RHS 157B veining.
*Length.*—0.8 cm.
*Width.*—0.8 cm.
*Shape.*—Orbicular.

Corolla:
*Form.*—Single, solitary, symmetrical; 5 imbricate petals.

Immature:
*Floret horizontal diameter.*—2.0 cm.
*Color upper petals, upper surface.*—RHS 157D.
*Color upper petals, lower surface.*—RHS 157D.

Mature:
*Floret horizontal diameter.*—2.5-3.0 cm.
*Floret length or depth.*—0.4 cm.
*Petal color, upper surface.*—RHS 155D but whiter; with a basal blush of RHS 143C and RHS 143B veining.
*Lower surface.*—RHS 155D but whiter; with a basal blush of RHS 143D and RHS 143C veining.
*Petal length.*—1.2 cm.
*Petal width petals.*—1.0 cm.
*Petal shape.*—Orbicular.
*Apex shape.*—Rounded to some broadly obtuse.
*Petal base shape.*—Attenuate.
*Margin.*—Entire.
*Petal texture, upper surface.*—Papillose.
*Lower surface.*—Papillose.

Sepals:
*Number of sepals.*—5.
*Color of sepals, upper surface.*—RHS 144B.
*Lower surface.*—RHS 144B.
*Length of sepals.*—0.5-0.6 cm.
*Width of sepals.*—0.3-0.4 cm.
*Sepal shape.*—Ovate.
*Apex shape.*—Acute.
*Margins.*—Entire.
*Texture, upper surface.*—Slightly pubescent.
*Lower surface.*—Glabrous.

Reproductive organs:
*Number of stamens.*—10.
*Filament color.*—RHS 150D.
*Filament length.*—0.5 cm.
*Filament diameter.*—Less than 0.1 cm.
*Anther color.*—RHS 150D.
*Anther length.*—0.15 cm.
*Anther shape.*—Oval, bi-lobed.
*Pollen color.*—RHS 14B.
*Pollen amount.*—Moderate.
*Pistil.*—2.
*Pistil length.*—0.3-0.4 cm.
*Style color.*—RHS 1B.
*Style length.*—0.2-0.3 cm.
*Stigma color.*—RHS 154D.
*Ovary color.*—RHS 151C.
*Ovary length.*—0.2 cm.
*Ovary width.*—0.3 cm.
*Fertility/seed set.*—Has not been observed on this hybrid.
*Disease/pest resistance.*—Has not been observed on this hybrid.

What is claimed is:

1. A new and distinct variety of *Saxifraga* plant named 'SAXZ0004' substantially as illustrated and described herein.

* * * * *